United States Patent
Krausman et al.

(10) Patent No.: US 6,878,121 B2
(45) Date of Patent: Apr. 12, 2005

(54) SLEEP SCORING APPARATUS AND METHOD

(76) Inventors: David T. Krausman, 1706 Pine Forest Ct., Bel Air, MD (US) 21014; Richard P. Allen, 110 Glen Oban Dr., Arnold, MD (US) 21012

( * ) Notice: Subject to any disclaimer, the term of this patent is extended or adjusted under 35 U.S.C. 154(b) by 240 days.

(21) Appl. No.: 10/287,253

(22) Filed: Nov. 1, 2002

(65) Prior Publication Data

US 2004/0087878 A1 May 6, 2004

(51) Int. Cl.$^7$ .......................... A61B 5/103; A61B 5/117
(52) U.S. Cl. ............................................. 600/587
(58) Field of Search ................................. 600/587, 509, 600/521, 595, 547

(56) References Cited

U.S. PATENT DOCUMENTS

| | | | |
|---|---|---|---|
| 4,353,375 A | 10/1982 | Colburn | 128/782 |
| 5,280,791 A * | 1/1994 | Lavie | 600/509 |
| 5,573,013 A | 11/1996 | Conlan | 128/782 |
| 5,749,372 A | 5/1998 | Allen-Krausman | 128/782 |
| 5,961,447 A | 10/1999 | Raviv-Weingarten | 600/300 |
| 5,999,846 A | 12/1999 | Pardey | 600/544 |
| 6,091,973 A | 7/2000 | Colla | 600/324 |
| 6,120,441 A | 9/2000 | Griebel | 600/300 |
| 6,142,950 A | 11/2000 | Allen-Krausman | 600/529 |
| 6,157,857 A | 12/2000 | Dimpfel | 600/544 |
| 6,171,258 B1 | 1/2001 | Karakasoglu et al. | 600/529 |
| 6,183,493 B1 | 2/2001 | Zammit | 606/196 |
| 6,241,686 B1 | 6/2001 | Balkin et al. | 600/544 |
| 6,306,088 B1 | 10/2001 | Krausman-Allen | 600/301 |
| 6,315,740 B1 | 11/2001 | Singh | 600/595 |
| 6,328,753 B1 | 12/2001 | Zammit | 606/196 |
| 6,392,962 B1 | 5/2002 | Wyatt | 368/107 |
| 2004/0049132 A1 * | 3/2004 | Barron et al. | 600/595 |

OTHER PUBLICATIONS

Allen & Krausman, *10$^{th}$ Annual Meeting, APPS*, p. 309; 1996.

* cited by examiner

*Primary Examiner*—Mary Beth Jones
*Assistant Examiner*—Brian Szmal
(74) *Attorney, Agent, or Firm*—Larry J. Guffey (57) ABSTRACT

A method and an apparatus are disclosed for scoring the quality of sleep experienced by a subject wearing the apparatus for a specified period. This sleep monitoring apparatus includes a motion sensor that quantifies the temporal variation in the subject's motion, an analog to digital converter to sample the sensor data, a microprocessor with embedded programmable memory to store control and processing firmware, a memory device for data storage, a display means, and a switch for staring and resetting the device. The firmware for this apparatus: (i) directs the microprocessor to sample sensor output at a prescribed time interval and to temporarily store this data in the memory device, (ii) directs the microprocessor to analyze the temporarily stored data to compute a sleep score based on the magnitude of movements recorded during the monitoring period, and (iii) controls the operation of the display means. Upon termination of the sleep period, the apparatus' display means will display a sleep score based on a scale of 0 to 100. A high score indicates restful sleep (very low movements), while a low score indicates excessive restlessness during the monitored sleep period.

20 Claims, 7 Drawing Sheets

SLEEP SCORING APPARATUS AND METHOD

BACKGROUND OF THE INVENTION

1. Field of the Invention

This invention relates to physiological monitoring and diagnostic testing devices and methods. More particularly, this invention relates to a device and method for monitoring levels of a person's arm movements during sleep and using this data to compute the person's "sleep score" based upon these movements.

2. Description of the Related Art

Sleep deprivation is almost always a component of an unbalanced lifestyle. In our fast-paced, chaotic society, the average adult in the United States sleeps 6.9 hours per night during the workweek, as opposed to the ideal 8 hours. More than fifty percent of Americans suffer from insomnia several nights a week. Many don't wake up feeling refreshed, and many experience sleepiness during daily activities like reading, watching TV, riding in a car, or sitting quietly after lunch.

Few realize the price they pay for cutting themselves short when it comes to sleep. Sleep deprivation is unhealthy for and is clearly associated with a variety of problems. Without proper sleep, people: (a) are more susceptible to illnesses and have a greater chance of experiencing emotional and mental health problems, (b) have a lower frustration tolerance and may tend to overreact when stresses occur in their lives, and (c) have diminished capacities to concentrate, remember, learn and complete tasks. Thousands die each year in automobile accidents that are the result of someone falling asleep at the wheel. There is even evidence that without proper sleep we accelerate aspects of the aging process and shorten our life span.

Although most are aware of the importance of a good night's sleep, there presently is no easy method of gauging just how well we actually do sleep. For most people, awareness of the quality of their sleep (i.e., how soundly they slept through the night) without a means of measurement is difficult, if not impossible.

Presently, there are two validated medical methods available to measure a person's sleep behavior. These methods are however, not intended to measure the quality of night-to-night sleep, but to identify sleep disorders such as insomnia, sleep apnea, the restless legs syndrome (RLS) and periodic limb movements (PLM).

The first method, the medically accepted gold standard, comprises comprehensive sleep testing utilizing polysomnography (PSG). This medical procedure involves a full night testing in a sleep laboratory to monitor the temporal variations in the amplitude of the patient's sleep-impacted, physiological parameters, including: a continuous measure of the level of oxygen saturation in the arterial blood flow (SpO2), heart rate, upper respiratory airflow, thorax and abdomen respiration efforts, electroencephalograms (EEG; electrical activity of the brain), electro-oculogram (EOG; electrical activity related to movement of the eyes), and electromyograms (EMG; electrical activity of a muscle).

The PSG testing procedures are expensive as they are typically conducted in clinical settings by trained PSG technician in attendance. Recently, more limited PSG monitoring procedures utilizing at least four physiological parameters has been shown to provide a reliable means of screening for sleep disorders. Typically, these limited procedures are administered in the home setting but require an attending PSG technician for the entire sleep night. Even more recently, advancements in limited PSG recording have resulted in some variations where the person is taught by a sleep professional to self-apply the sensors and electrodes which are tethered to physiological recorders. The results are then viewed and evaluated by a sleep professional.

A second less complex method for assessing both sleep behavior (i.e., extent of sleep versus wake state during the sleep period) and screening for sleep disorders is by actigraphy means. Like PSG, this is a medical sleep testing procedure that requires the instrument to be cleared for use by the FDA and can only be used under the direction of a sleep professional. Additionally, since an actigraphy is typically used as tool for diagnosing sleep disorders and monitoring treatment of the disorder, the device can only be purchased by prescription.

Actigraphy methods utilize a wrist-worn actigraph recording device and associated sleep analysis software. The actigraph recorder, first described by Colburn et. al. in 1976 and later patented in 1982 (U.S. Pat. No. 4,353,375) captures arm movements by means of an accelerometer sensor. The device stores accumulated activity data, identified as activity counts, in pre-set time epochs of 30, 60 or 120 seconds. This information is then download to an external computer for graphical display and analysis.

The software for this analysis requires a complex, multipass analysis program. An example of this type of program was presented by the present inventors' at the 10th Annual Meeting, *APPS*, Abstract No. 309, 1996; where a three-pass, computer algorithm is used to score arm activity data (activity counts) recorded in thirty second epochs and downloaded from an actigraph device (i.e., an "ActiTrac" monitor which is manufactured by IM Systems, Baltimore, Md.).

The first pass in this analysis identifies whether one was in a sleep or wake state during a particular 30-second epoch according to the following formula:

$$A+B+E \geq K \text{ (a constant, which is set to 18), identified as a wake state epoch "<18, identified as a sleep state epoch}$$

where:
E=the activity count for the current epoch in question,
A=the sum of the activity counts for the four epochs preceding the current epoch, B=the sum of the activity counts for the four epochs following the current epoch.

The second pass in this analysis uses an algorithm that is designed to identify movement artifacts due to brief arousals and the sleep hysteresis effect. Artifacts are defined as any situation in which, for a given epoch: $(A+B+E) \geq 18$ and $(A+B)=0$. Identification of such events resulted in the activity count of the target epoch being re-coded as "0."

The third pass in this analysis conducts a recalculation of sleep-wake states for those epochs affected by the second pass change, which would be the four epochs both preceding and following the current epoch.

The logic behind this sleep/wake scoring algorithm assumes that a subject is asleep when no arm movements are present. When a short burst of movement is detected, for example when the subject rolls over in bed, such activity is classified as an "arousal". When there is a long burst of movement, the person is considered to be fully awake.

Thus, this sleep scoring program scores a fully asleep condition when there are three consecutive minutes of low arm activity, and conversely, the subject is assumed to be in the awake state when three consecutive minutes of high activity are detected. The final actigraphy sleep score compares the measured awake-time to the measured sleep-time and computes the results in terms of a sleep efficiency percentage (0–100%).

The less-than-desirable features of such actigraphy methodology include: 1) the equipment used is very expensive, a typical system including wrist recorder, download interface and analysis software ranges from approximately $2,000 (for an "ActiTrac" device from IM Systems) to $4,000 (for a "Mini-Motionlogger" from Ambulatory Monitoring, Ardsley, N.Y.), 2) its data must be downloaded to an external computer for analysis, 3) the use of the system requires administration and analysis by a skilled sleep professional, and 4) actigraphy recorders must be FDA cleared as class II devices, and can only be purchased by a sleep professional with a prescription, 5) its hardware is designed to detect sleep disorders by means of a sleep efficiency score, and 6) its equipment is not appropriate for home use by those who might wish to measure their night-to-night quality of sleep.

A need therefore exists for an alternative form of sleep monitoring that can provide the non-professional with an easy and inexpensive method of monitoring their own sleep performance in the privacy of their own bedroom. The present invention ideally serves this need.

OBJECTS AND ADVANTAGES

There has been summarized above, rather broadly, the prior art that is related to the present invention in order that the context of the present invention may be better understood and appreciated. In this regard, it is instructive to also consider the objects and advantages of the present invention.

It is an object of the present invention to provide an easy means for one to gauge how well he or she is actually sleeping.

It is another object of the present invention to provide a device that is reasonably accurate, compact, and easy to use, and that provides an immediate visual feedback score of nightly sleep performance.

It is an object of the present invention to provide a device that provides, without having to download the device's data to a base computer, an immediate visual feedback score of nightly sleep performance.

It is yet another object of the present invention to provide a sleep measuring device that does not require for its use the guidance of a sleep professional.

It is a further object of the present invention to provide a method that one can use to gauge how well he or she is actually sleeping.

It is an object of this present invention to use the measurement and computation of arm movements per hour as a means to calculate and display a scale representative of a user's sleep performance.

These and other objects and advantages of the present invention will become readily apparent as the invention is better understood by reference to the accompanying summary, drawings and the detailed description that follows.

SUMMARY OF THE INVENTION

Recognizing the need for a much simpler device and method for assessing one's sleep, the present invention is generally directed to satisfying the needs set forth above and the problems identified with prior systems for assessing one's sleep.

In accordance with one preferred embodiment of the present invention, the foregoing need can be satisfied by providing a sleep meter or sleep scoring apparatus comprising: (1) a motion sensor that quantifies the temporal variation in the subject's motion at the sensor's location, (2) an analog to digital converter to sample the sensor data, (3) a microprocessor with embedded programmable memory to store control and processing firmware, (4) a memory device for data storage, (5) a display means, and (6) a switch for resetting the device, wherein the firmware: (i) directs the microprocessor to sample sensor output at a prescribed time interval and to temporarily store this data in the memory device, (ii) directs the microprocessor to analyze the temporarily stored data to compute a sleep score based on the magnitude of movements recorded during the monitoring period, and (iii) controls the operation of the display means.

Worn like a wristwatch, the apparatus samples and quantifies the motion of the arm to determine a ratio of arm movements to non movements during the sleep period. The sleep period or sleep time being defined as: the time of reset to the time of termination as controlled by the user by means of the push-button switch. Upon termination of the sleep period, the apparatus' display means will display the final score based on a scale of 0 to 100. A high score indicates restful sleep (very low arm movements), while a low score indicates excessive restlessness. Each score is automatically saved in memory for recall on the display means.

Thus, there has been summarized above, rather broadly, the more important features of the present invention in order that the detailed description that follows may be better understood and appreciated. There are, of course, additional features of the invention that will be described hereinafter and which will form the subject matter of any eventual claims to this invention.

In this respect, before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF THE PREFERRED EMBODIMENT

Sleep research studies (e.g., by Gorny, Allen, Krausman, et al., *Sleep Research*, 1997; Gorny and Allen, *Sleep*, 1999; Verbeek, et al., *Perceptual Motor Skills*, 2001) have shown that fewer arm movements during sleep relate to more restful sleep, while excessive movements are associated with restless or poorer sleep.

The present invention therefore uses this finding to develop a sleep meter or sleep monitoring apparatus. It operates by monitoring by acceleration methods a person's arm movements to yield a sleep score for the person's sleep behavior during the monitored period.

Figure 1:
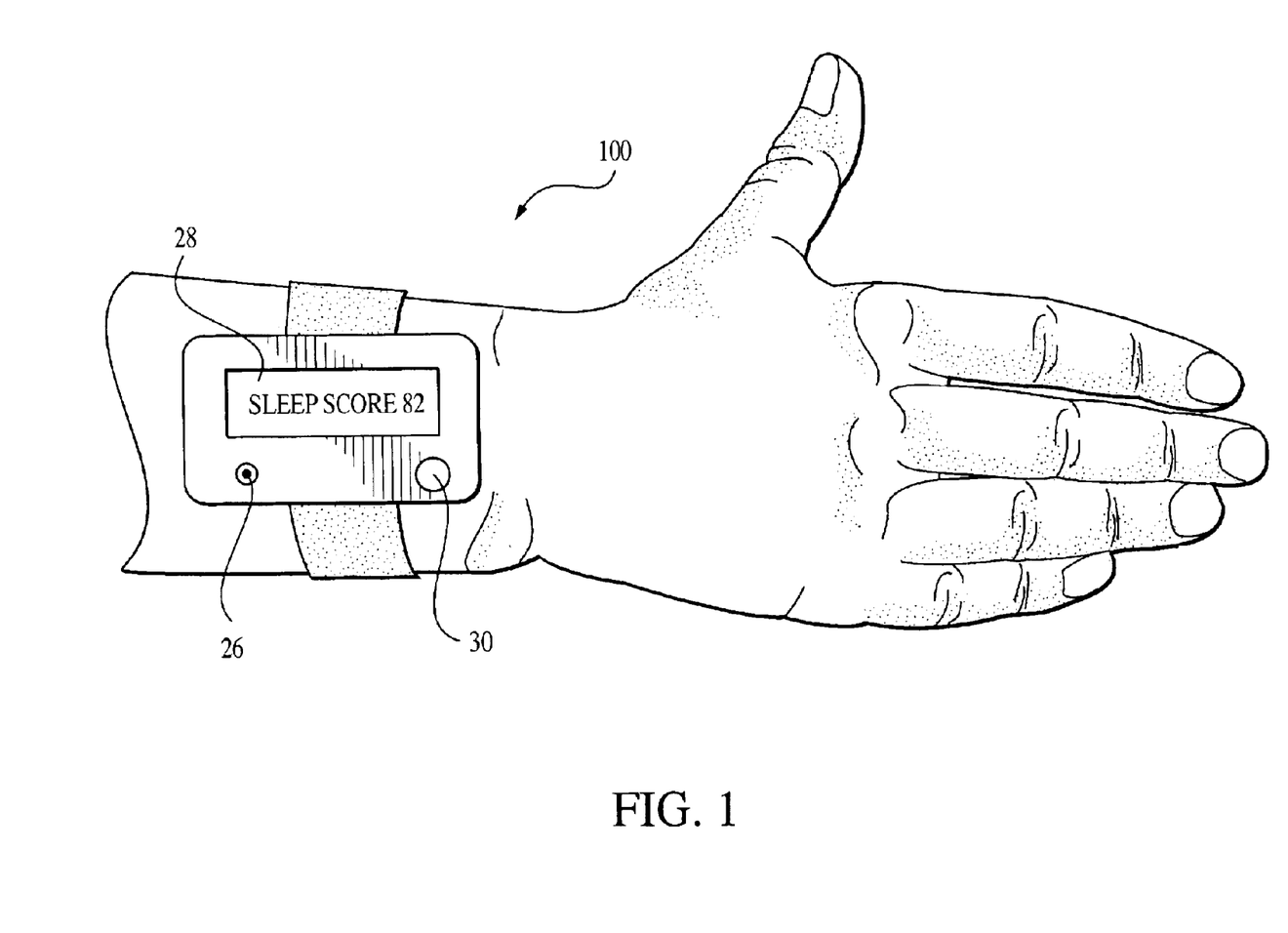
FIG. 1 illustrates approximate placement at the wrist of a preferred embodiment of the present invention.

In a preferred embodiment, the present invention takes the form of a sleep meter 10 that is worn on the wrist. Using digital sampling techniques, it measures the intensity and duration of arm movements. The value it measures is then scaled and visually presented to the user as a sleep score ranging from 0 to 100. See FIG. 1, wherein like reference numerals designate like elements throughout all the drawings.

Figure 2:
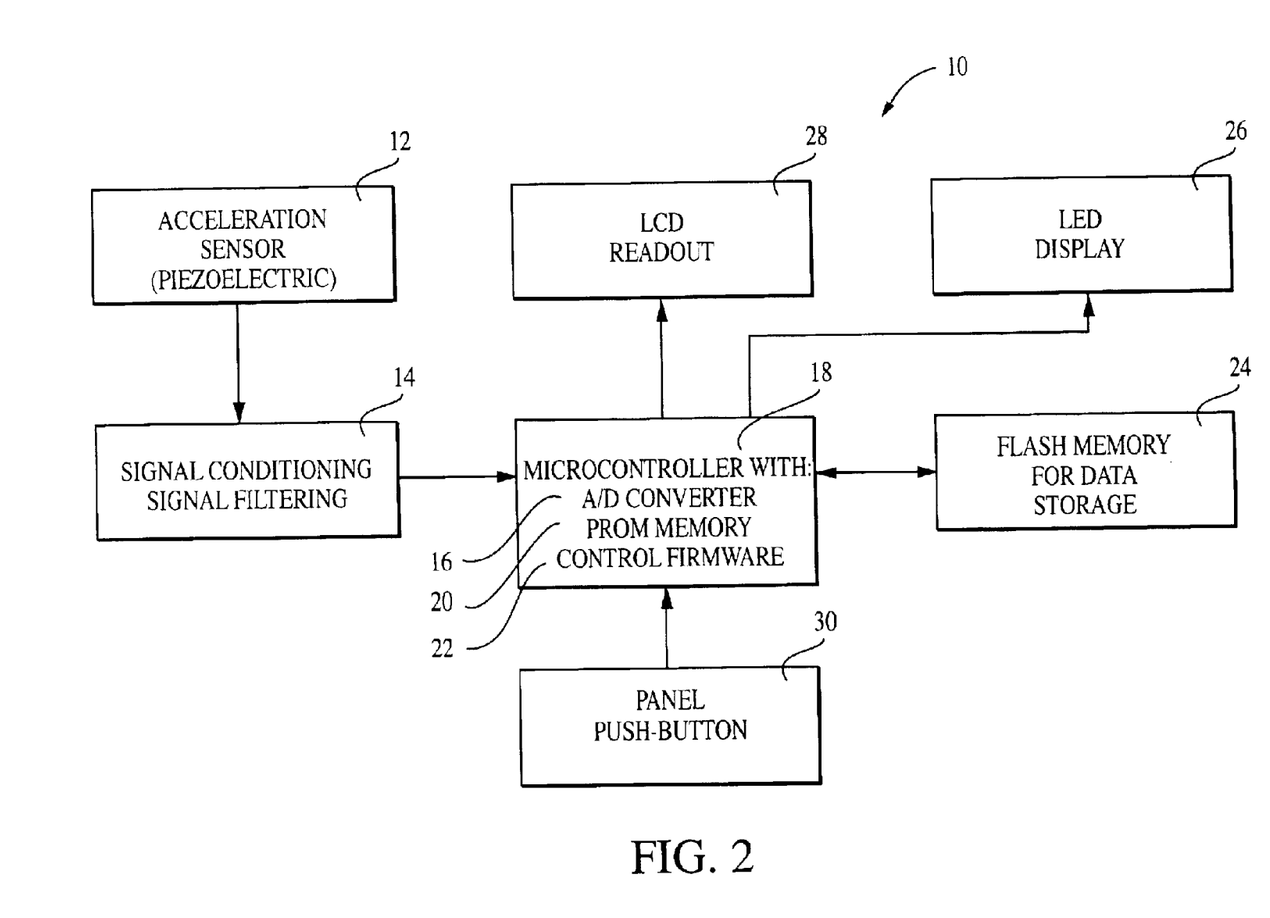
FIG. 2 is a schematic flow diagram of a preferred embodiment of the present invention.

A schematic block diagram of this device is shown in FIG. 2. It is a battery operated device that consists of: (1) a piezoelectric motion sensor 12 with appropriate signal conditioning and filtering circuitry 14 to yield required levels of signal fidelity, thus providing sensor output data that quantifies the temporal variations in the amplitude and frequency of subject's arm movements, (2) an analog to digital converter 16 to sample sensor output data at a sampling frequency that is sufficient to encompass the frequency range of movements expected at the selected measurement site, (3) a microprocessor 18 with embedded programmable memory 20 to store control and processing firmware 22, including appropriate algorithms to compute a sleep score based on movement data provided by the piezoelectric motion sensor 12, (4) memory device 24 for storing the movement data, (5) an LED 26 that flashes each time a preset cumulative value of arm movements are obtained during the recording session, (6) an LCD 28 readout that is: (i) incremented one count for each LED flash during the recording session, (ii) displays the sleep score at termination of the sleep period, and (iii) displays sleep scores stored from previous recording sessions, and (7) a panel switch 30 that: (i) resets the device when depressed for three seconds or longer, (ii) then terminates the recording session when momentarily pressed, (iii) initiates recall of previous sleep scores, and (iv) clears all memory when depressed for ten seconds or longer.

Figure 3:
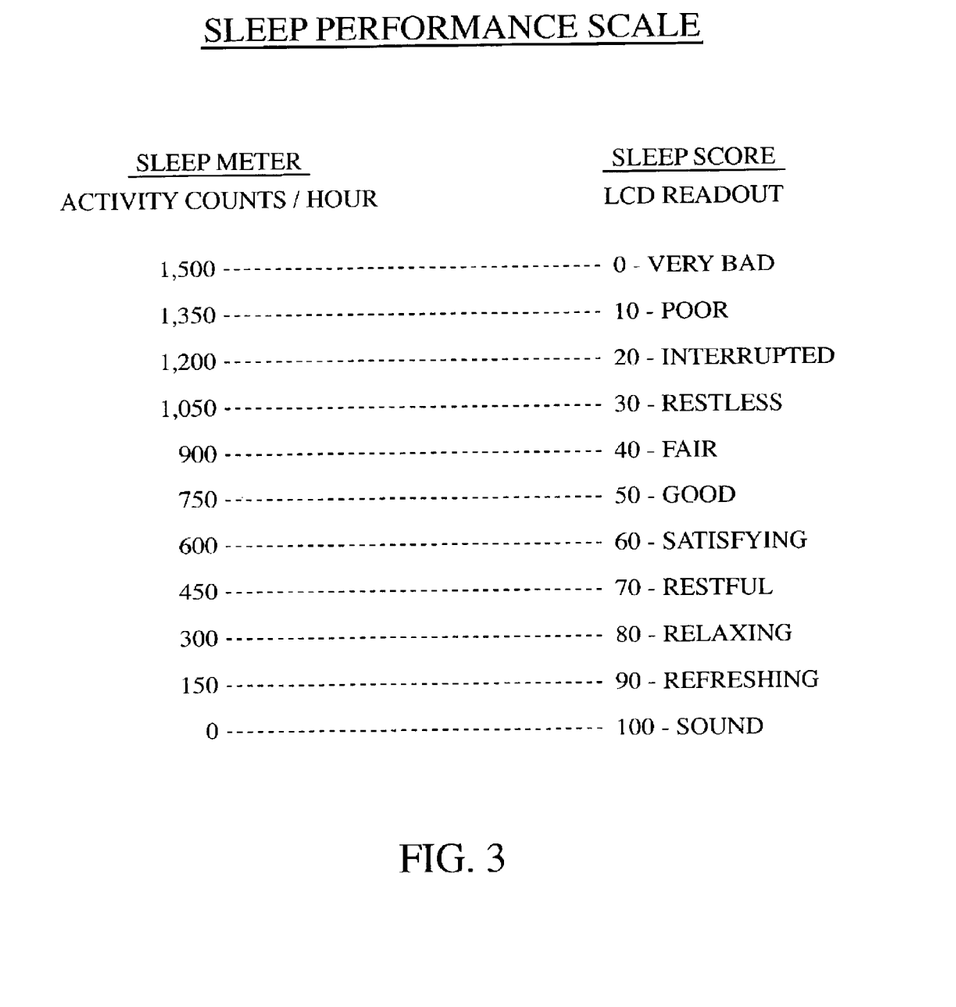
FIG. 3 shows arm movement activity calibrated in units of activity counts per hour and the calibration of this data with a sleep performance scale.

The sleep period of the present invention can range from minutes to hours, with the resulting score based on the magnitude of arm movements recorded during the monitoring period. As shown in FIG. 3, a sleep score between 90–100 represents sound and refreshing sleep, while 70–80 relates to relaxing and relaxing sleep. A score of 30–40 is seen to equal fair to restless sleep, and a low score from 0–10 is indicative of poor to very bad sleep performance.

Worn like a wristwatch, the sleep meter is extremely easy to use. Upon reset, data is cleared and the meter is activated. A small green LED located on the front panel of the meter will flash each time a preset cumulative value of arm movements is achieved. The LCD readout is also incremented one count for each LED flash. This visual feedback verifies that the meter is in the active recording mode and working properly. When the user awakens, a momentary press of the push-button will initiate the computation of the sleep score and present the results on the LCD readout. Subsequent short presses will retrieve and display sleep scores from previous sleep periods. All data (both current and memory), will be cleared by pressing the front panel push-button for ten seconds or longer.

Figure 4A:
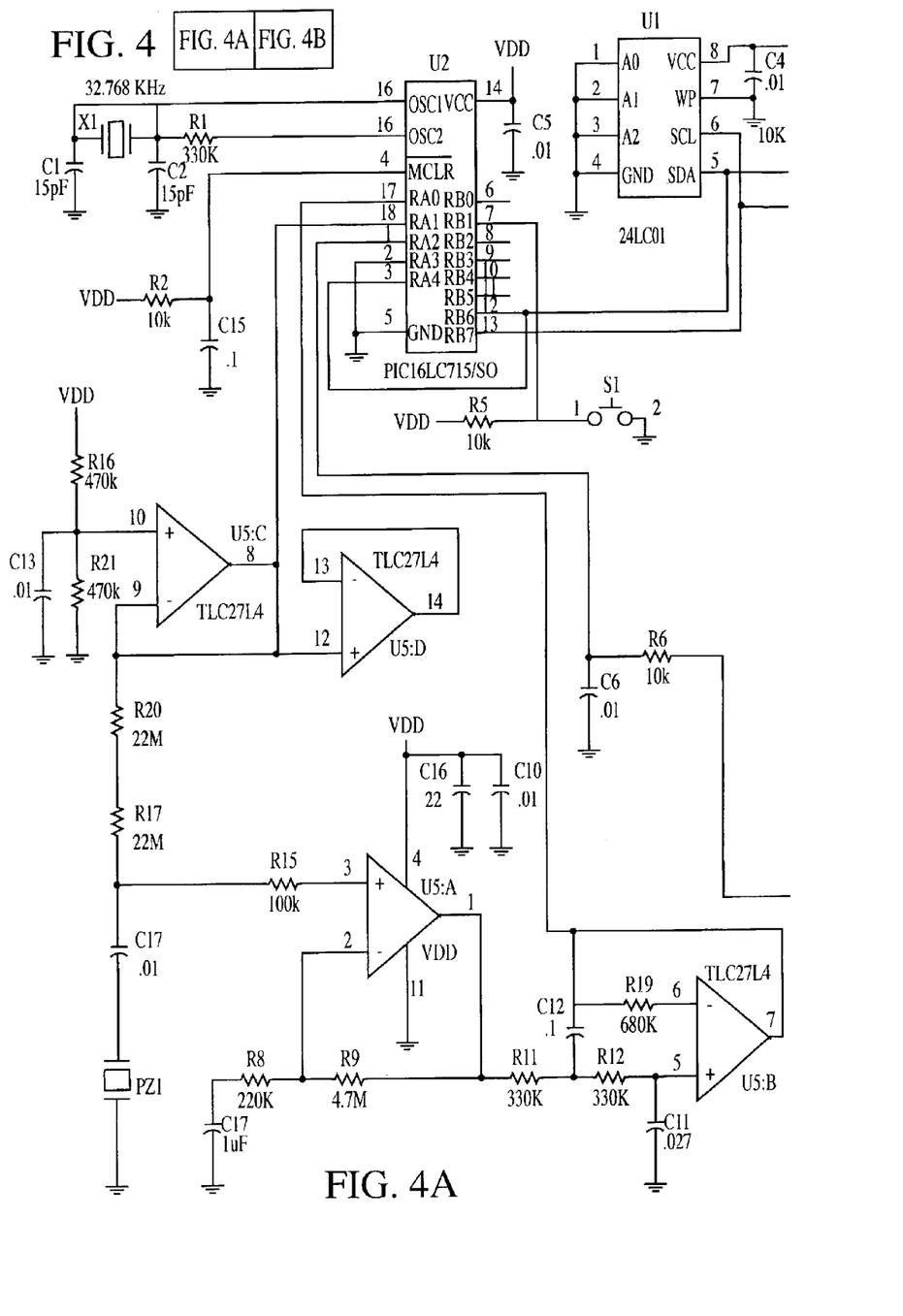
FIG. 4A–4B display a schematic circuit diagram of the embodiment shown in FIG. 2.
Figure 4B:
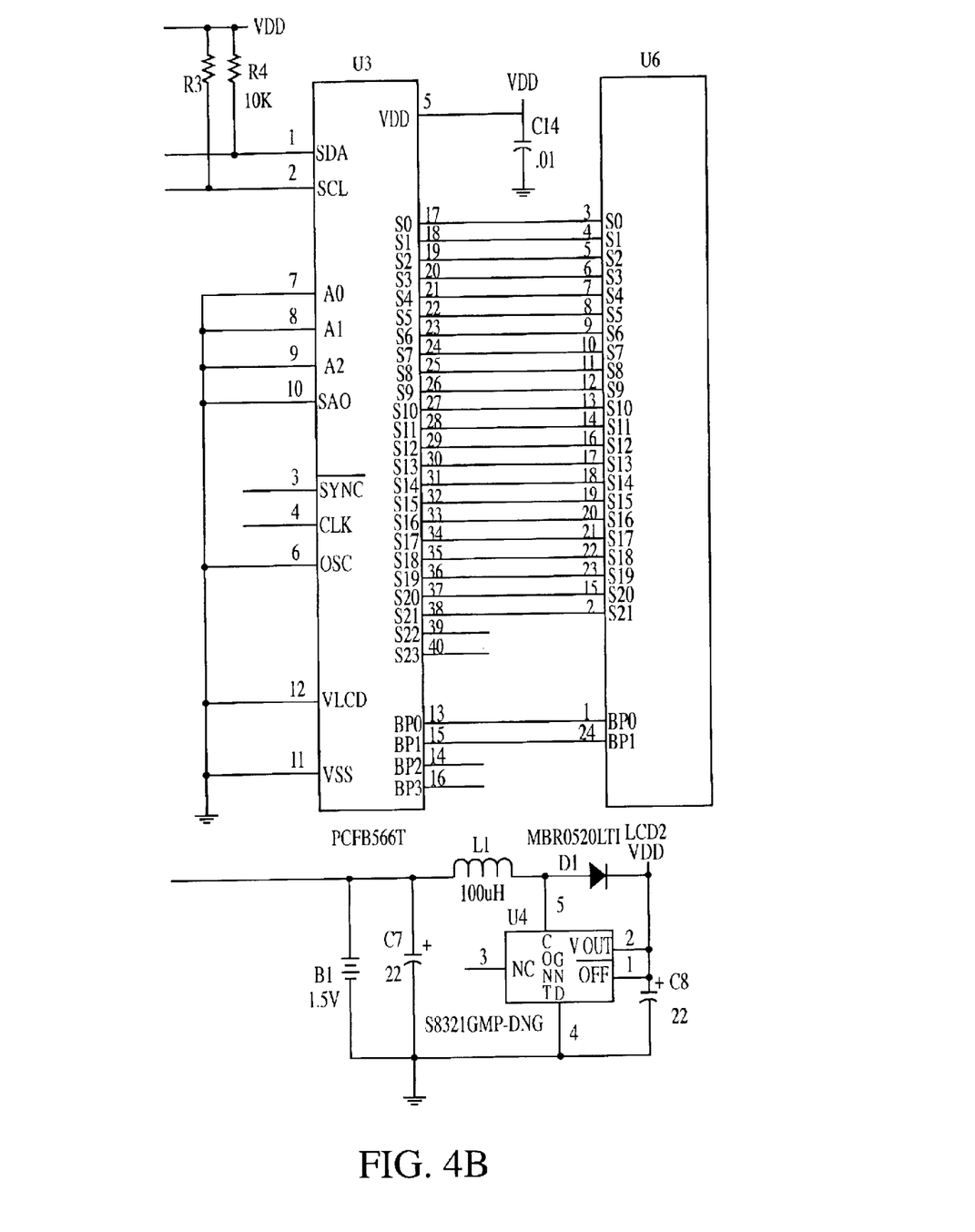

Additional appropriate hardware for use in the present invention is shown in FIG. 4A–4B. It includes: (1) printed circuit boards of four-layer, through-hole design for surface mount technology (SMT) components, (2) an ultra-low power CMOS microprocessor (Microchip PIC 16C715 microprocessor or similar) with support chips for timing, control and with programmable nonvolatile FLASH memory, the microprocessor containing: (i) an analog to digital converter for digitizing the acceleration signal produced by the piezoelectric motion sensor, (ii) firmware for the microprocessor to receive the movement data, (iii) firmware for storing the real-time sampled data (typically once per 31.25 milliseconds), (iv) firmware for computation of the movement activity per unit time, (iv) firmware for computation of the final sleep score, (v) output control to flash the LED display, and (vi) output control to display the final sleep score on the LCD, (3) a push button switch to: (i) reset and start the device, (ii) clear data, and (iii) provide recall of stored data, and (4) a replaceable AAA battery cell providing ample power for a minimum of one hundred twenty recording sessions of eight hour duration.

The inventors' methods for detecting and quantifying physical motion by acceleration methods have previously been described in U.S. Pat. No. 5,749,372. These methods are further improved upon herein to measure and record arm movement activity during the sleep period, thus providing, at the termination of the sleep period, an immediate visual score relating to the level of one's arm movements measured during the sleep period.

Figure 5:
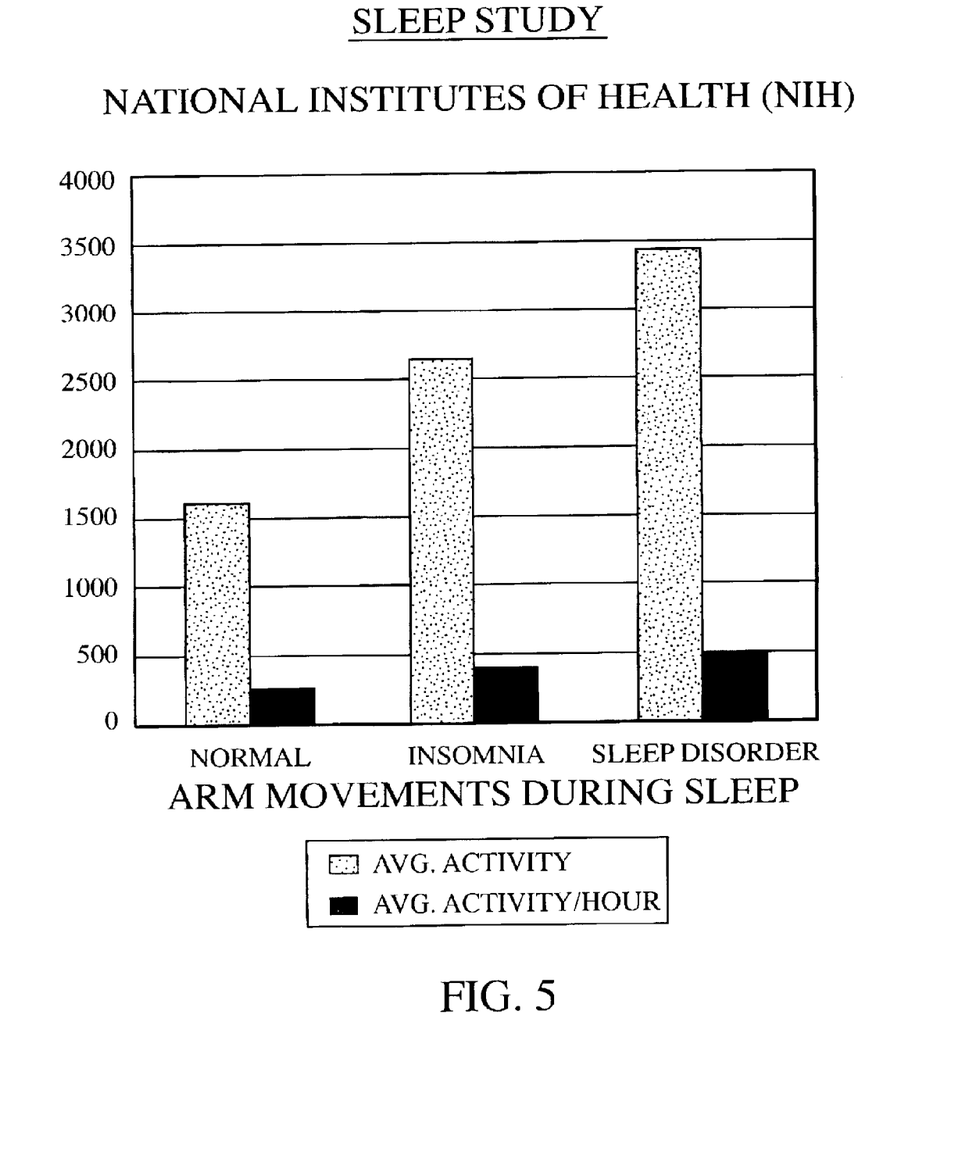
FIG. 5 displays the activity counts recorded for populations characterized by having sleep that may be classified as either normal, insomnia or sleep disorder.

The method described in this present invention for calculating a sleep score has been validated by data derived from a clinical sleep study (N44-NS-8-2328) sponsored by the National Institutes of Health (NIH). In this study, twenty-six subjects including nine normals, nine insomniacs and eight with the restless legs syndrome were subjected to an over-night clinical sleep session (typically ranging from 5 to 8 hours). Arm movements were recorded by means of an Actigraph device and scored for sleep efficiency by means of the algorithm described above. See FIG. 5.

The raw activity data from the actigraph represented both total arm movements and movements per hour for the sleep night. This data from the above clinical sleep study was then used to establish a calibration factor for the sleep meter, where one activity count is equal to a movement acceleration of 0.0066 g per second. Utilizing this calibration factor, the sleep meter and corresponding sleep scale were developed thus providing a new, less-complex method of calculating a sleep score as used in this present invention.

As shown in FIG. 3, a new scoring scale and method is established where 1,500 activity counts per hour recorded by the present invention is equivalent to the worst-case score of zero. A high count of 1,500 represents excessive arm movements that would be indicative of a sleep-disordered patient and scored as very bad sleep. Conversely, an activity count of zero per hour would yield a score of 100, which is indicative of perfect sound sleep. Accordingly, an activity count of 750 per hour would produce a sleep score of 50 which relates to good sleep as seen on the Sleep Performance Scale of FIG. 3.

Figure 6:
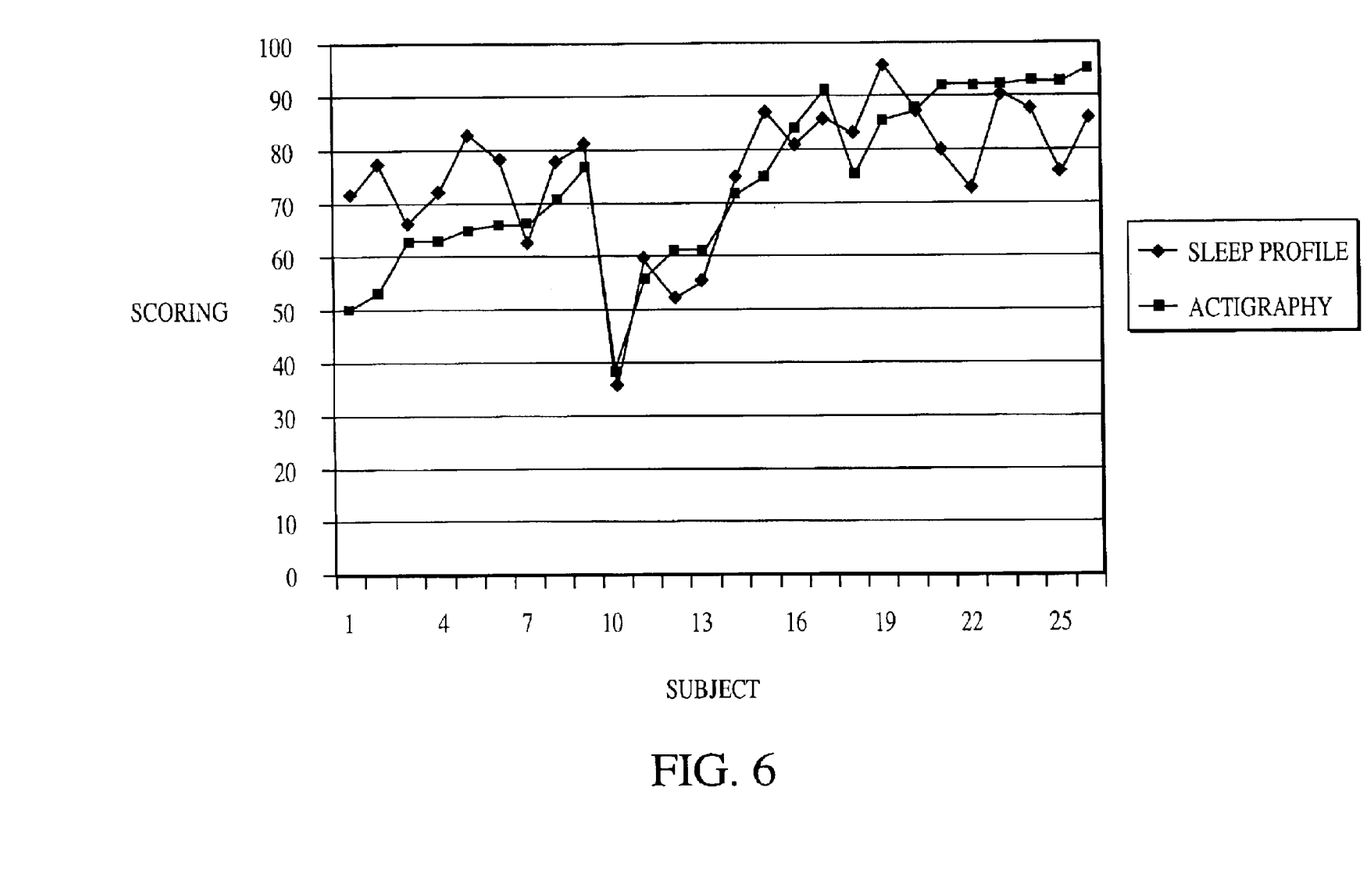
FIG. 6 compares sleep scores calculated with the present invention with those determined by actigraphy.

The data results (sleep scores) derived from all twenty six subjects, were then computed by this present invention and compared to the sleep/wake efficiency scores determined by actigraphy. This comparison yielded an average agreement of 85%. See FIG. 6. This high correlation with establish sleep-wake efficiency scores computed by actigraphy, therefore validates the accuracy of the developed sleep scoring scale for the present invention.

As noted above, this device also contains a recall function to sequentially view the sleep score results of previous sleep periods. The invention therefore allows a non-professional, lay person (consumer) to track their night-to-night sleep performance in the home setting and in the comfort of their own bed. With this present invention, a person can make simple adjustments to their daily lifestyles such as better exercise and diet to help enrich sleep habits and to enhance their sleep performance, thus helping to decrease daytime drowsiness and improve overall health and well being.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. A sleep monitoring apparatus for scoring the quality of sleep experienced by a subject wearing said apparatus for a specified period, said sleep monitoring apparatus comprising:
   a means for sensing the temporal variation in the motion at the location where said apparatus is being worn,
   an analog to digital converter connected to said sensing means for sampling the data sensed by said motion sensing means,
   a microprocessor connected to said converter, said microprocessor having embedded programmable memory,
   a means connected to said microprocessor for storing data,
   a display means connected to said microprocessor, and
   firmware that controls the operation of said apparatus by directing the microprocessor to sample the output of said sensing means at a prescribed time interval and to temporarily store said sampled data in said data storage means, by directing the microprocessor to analyze the temporarily stored data to compute a sleep score based on the magnitude of movements recorded during said monitoring period, and by controlling the operation of said display means to display said sleep score.

2. A sleep monitoring apparatus as recited in claim 1, further comprising a means connected to said microprocessor for resetting and starting the operation of said apparatus.

3. A sleep monitoring apparatus as recited in claim 1, wherein said apparatus is adapted to be worn on a subject's arm.

4. A sleep monitoring apparatus as recited in claim 2, wherein said apparatus is adapted to be worn on a subject's arm.

5. A sleep monitoring apparatus as recited in claim 1, wherein said firmware controls sampling of said output of said motion sensing means so as to sample at a sampling frequency that encompasses the frequency range of movements expected at the location where said apparatus is worn.

6. A sleep monitoring apparatus as recited in claim 4, wherein said firmware controls sampling of said output of said motion sensing means so as to sample at a sampling frequency that encompasses the frequency range of movements expected at the location where said apparatus is worn.

7. A sleep monitoring apparatus as recited in claim 1, wherein said firmware controls computation of said sleep score by utilizing an algorithm that relates movement counts per specified time period to one of a specified number of levels that are defined as comprising said sleep score.

8. A sleep monitoring apparatus as recited in claim 6, wherein said firmware controls computation of said sleep score by utilizing an algorithm that relates movement counts per specified time period to one of a specified number of levels that are defined as comprising said sleep score.

9. A sleep monitoring apparatus as recited in claim 1, wherein said motion sensing means is a piezoelectric motion sensor having signal conditioning and filtering circuitry is to yield specified levels of signal fidelity.

10. A sleep monitoring apparatus as recited in claim 8, wherein said motion sensing means is a piezoelectric motion sensor having signal conditioning and filtering circuitry to yield specified levels of signal fidelity.

11. A method for scoring the quality of sleep experienced by a subject during a specified period, said method comprising the steps of:
    locating a sleep monitoring apparatus at a prescribed location on said subject, said apparatus having a motion sensing means, an analog to digital converter, a microprocessor having embedded programmable memory, a data storage means, a display means, and firmware that controls the operation of said apparatus,
    sampling the output of said sensing means at a prescribed time interval,
    temporarily storing said sampled data in said data storage means,
    analyzing said temporarily stored data to compute a sleep score based on the magnitude of movements recorded during said monitoring period, and
    displaying on display means the value of said computed sleep score.

12. A method as recited in claim 11, wherein said apparatus further having a means connected to said microprocessor for resetting and starting the operation of said apparatus.

13. A method as recited in claim 11, wherein said apparatus is adapted to be worn on a subject's arm.

14. A method as recited in claim 12, wherein said apparatus is adapted to be worn on a subject's arm.

15. A method as recited in claim 11, wherein said firmware controls sampling of the output of said motion sensing means so as to sample at a sampling frequency that encompasses the frequency range of movements expected at the location where said apparatus is worn.

16. A method as recited in claim 14, wherein said firmware controls sampling of the output of said motion sensing means so as to sample at a sampling frequency that encompasses the frequency range of movements expected at the location where said apparatus is worn.

17. A method as recited in claim 11, wherein said firmware controls computation of said sleep score by utilizing an algorithm that relates movement counts per specified time period to one of a specified number of levels that are defined as comprising said sleep score.

18. A method as recited in claim 16, wherein said firmware controls computation of said sleep score by utilizing an algorithm that relates movement counts per specified time period to one of a specified number of levels that are defined as comprising said sleep score.

19. A method as recited in claim 11, wherein said motion sensing means is a piezoelectric motion sensor having signal conditioning and filtering circuitry to yield specified levels of signal fidelity.

20. A method as recited in claim 18, wherein said motion sensing means is a piezoelectric motion sensor having signal conditioning and filtering circuitry to yield specified levels of signal fidelity.

* * * * *